United States Patent
Lu

(10) Patent No.: US 9,931,294 B2
(45) Date of Patent: Apr. 3, 2018

(54) STABLE SKIN CARE COMPOSITION HAVING COSMETICALLY ACCEPTABLE OILS

(71) Applicant: L'OREAL, Paris (FR)

(72) Inventor: Gloria Lu, Rahway, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/982,630

(22) Filed: Dec. 29, 2015

(65) Prior Publication Data

US 2017/0181959 A1   Jun. 29, 2017

(51) Int. Cl.
| | |
|---|---|
| A61K 8/92 | (2006.01) |
| A61K 8/37 | (2006.01) |
| A61K 8/35 | (2006.01) |
| A61Q 17/04 | (2006.01) |
| A61K 8/40 | (2006.01) |

(52) U.S. Cl.
CPC ............... *A61K 8/922* (2013.01); *A61K 8/35* (2013.01); *A61K 8/37* (2013.01); *A61K 8/375* (2013.01); *A61K 8/40* (2013.01); *A61Q 17/04* (2013.01); *A61K 2800/592* (2013.01)

(58) Field of Classification Search
CPC ... A61K 8/37; A61K 8/35; A61K 8/06; A61K 8/345; A61K 8/39; A61K 8/678; A61K 8/86; A61Q 17/04; A61Q 19/00
See application file for complete search history.

(56) References Cited

U.S. PATENT DOCUMENTS

| | | | | |
|---|---|---|---|---|
| 5,047,232 A | * | 9/1991 | Kaplan | A61K 8/39 424/59 |
| 5,397,497 A | | 3/1995 | Jakobson et al. | |
| 2005/0142080 A1 | * | 6/2005 | Goppel | A61Q 17/04 424/59 |
| 2011/0014139 A1 | * | 1/2011 | Viala | A61K 8/87 424/59 |
| 2013/0136701 A1 | * | 5/2013 | Kasai | A61Q 17/04 424/43 |

FOREIGN PATENT DOCUMENTS

| | | | | |
|---|---|---|---|---|
| EP | 1709952 B1 | 10/2012 | | |
| WO | 0162217 A2 | 8/2001 | | |
| WO | WO 2014098264 A1 | * 6/2014 | ............... | A61K 8/37 |

* cited by examiner

*Primary Examiner* — Mark V Stevens

(74) *Attorney, Agent, or Firm* — McNees Wallace & Nurick LLC

(57) ABSTRACT

A skin care composition including a cosmetically acceptable oil, from about 0.25% to about 7.0%, based upon the weight of the composition, of a polyglyceryl fatty acid ester surfactant having an hydrophile-lipophile balance value of from about 9 to about 12, and a sunscreen active. The composition is stable.

18 Claims, No Drawings

STABLE SKIN CARE COMPOSITION HAVING COSMETICALLY ACCEPTABLE OILS

FIELD OF THE INVENTION

The present invention is directed to a stable skin care composition having a cosmetically acceptable oil and methods for producing same. More specifically, the present invention is directed to a stable skin care composition having cosmetically acceptable oil, sunscreen actives and polyglyceryl fatty acid ester surfactants, for application onto a keratinous substrate for UV protection.

BACKGROUND OF THE INVENTION

Facial treatment oil popularity has risen dramatically in the recent years. It is desirable to include natural oils, such as evening primrose oil, almond oil, and coconut oil into these products, as they contain naturally moisturizing fatty acids. However, a drawback of known facial oil products are the inherently greasy, oily texture. Such greasy, oily textures may be undesirable to consumers.

Conventional sunscreen products generally take the form of ultraviolet (UV)-filter compounds and/or particulate UV-screening compounds (collectively, "sunscreen actives") that are solubilized, emulsified, or dispersed in a vehicle, which is topically applied to the skin.

While it is desirable to utilize natural oils and sunscreen actives into topically applied compositions for skin care or sunscreen compositions, the incorporation of these components has posed various stability challenges. Examples of lack of stability include discoloration of the formula and/or precipitation of the ingredients out of the composition. In particular, liposoluble UV filters present a challenge for incorporation into emulsions intended for topical application onto a keratinous substrate, as most traditional emulsions are thickened and/or stabilized with natural or synthetic polymers, such as gums and polyacrylates, which are very sensitive to electrolytes.

There remains a need to provide a composition, including skin care and sunscreen compositions, capable of stably carrying natural oils and/or sunscreen actives, which is also tactilely pleasing to consumers upon application.

BRIEF SUMMARY OF THE INVENTION

In an exemplary embodiment, a composition in the form of a stable skin care composition including a cosmetically acceptable oil, from about 0.25% to about 5.0%, based upon the weight of the composition, of a polyglyceryl fatty acid ester surfactant having a hydrophile-lipophile balance value of from about 9 to about 12, and a sunscreen active.

In another exemplary embodiment, a method for preparing the composition is provided involving mixing the above-disclosed ingredients to form the composition.

The present disclosure is also directed to a method for cosmetic treatment of keratinous tissues by applying the above-disclosed composition onto a surface of the keratinous tissue.

Other features and advantages of the present invention will be apparent from the following more detailed description of the preferred embodiment which illustrates, by way of example, the principles of the invention.

DETAILED DESCRIPTION OF THE INVENTION

All numbers expressing quantities of ingredients and/or reaction conditions are to be understood as being modified in all instances by the term "about", unless otherwise indicated.

"Keratinous tissue," as used herein, includes, but is not limited to, skin, hair, and nails.

"Homogenous" means having the visual appearance of being substantially uniform throughout, i.e., visually appears as a single phase emulsion.

It has been surprisingly and unexpectedly discovered by the inventors that the use of low levels of certain polyglyceryl fatty acid ester surfactants in an oil containing composition having UV protective properties, yields exceptional stability and skin absorption properties.

Cosmetically Acceptable Oil

The composition according to the invention may comprise at least one cosmetically acceptable oil. The oil that may be used in the present invention may be chosen, alone or as a mixture, from:

(a) hydrocarbon-based oils of animal origin;
(b) hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, quinoa oil, rye oil, safflower oil, candlenut oil, passionflower oil or musk rose oil; shea butter; or caprylic/capric acid triglycerides, for instance those sold by the company Stéarineries Dubois or those sold under the names Miglyol 810®, 812® and 818® by the company Dynamit Nobel;
(c) ethers containing from 10 to 40 carbon atoms;
(d) linear or branched hydrocarbons of mineral or synthetic origin, such as petroleum jelly, polydecenes, hydrogenated polyisobutene such as Parleam®, squalane and liquid paraffins, and mixtures thereof;
(e) esters, for instance oils of formula $R_1COOR_2$ in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2 10$, for instance dicaprylyl carbonate, purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, or alcohol or polyalcohol heptanoates, octanoates, decanoates or ricinoleates, for instance propylene glycol dioctanoate; hydroxylated esters, for instance isostearyl lactate, diisostearyl malate or 2-octyldodecyl lactate; polyol esters and pentaerythritol esters;
(f) fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol, and (g) higher fatty acids such as oleic acid, linoleic acid or linolenic acid, and mixtures thereof.

The cosmetically acceptable oils that may be used in the composition according to the invention may be non-volatile polydimethylsiloxanes (PDMS), polydimethylsiloxanes comprising alkyl or alkoxy groups, which are pendent and/or at the end of a silicone chain, these groups each contain from 2 to 24 carbon atoms, phenyl silicones, for instance phenyl trimethicones, phenyl dimethicones, phenyltrimethyl-siloxydiphenylsiloxanes, diphenyl dimethicones and diphenyl-methyldiphenyltrisiloxanes, and mixtures thereof.

In one embodiment, the composition according to the present invention includes a combination of synthetic esters and natural oils.

The cosmetically acceptable oil is typically present in the composition in an amount of from about 10% to about 90% by weight, preferably from about 30% to about 70% by weight, and more preferably from about 50% to about 65% by weight, based on the total weight of the composition.

Polyglyceryl Fatty Acid Ester Surfactant

The composition according to the invention may comprise at least one polyglyceryl fatty acid ester surfactant. The polyglyceryl fatty acid ester surfactant, according to the present invention, is a polyglyceryl fatty acid ester surfactant having a hydrophile-lipophile balance of between about 9 and about 12. It has surprisingly and unexpectedly been discovered that the use, in particular, of polyglyceryl fatty acid ester surfactants having a hydrophile-lipophile balance of between about 9 and about 12 facilitates the formation of stable oil compositions, from both a chemical and physical perspective.

Suitable polyglyceryl fatty acid ester surfactants include, but are not limited to, the following:

polyglyceryl-2 laurate, in particular, as sold by TAIYO KAGAKU under the name Sunsoft Q-12D-C;

polyglyceryl-10 dioleate, in particular, as sold by TAIYO KAGAKU under the name Sunsoft Q-172Y-C; and/or polyglyceryl-6 dicaprate, in particular, as sold by TAIYO KAGAKU under the name Sunsoft Q-102H-C.

polyglyceryl-6 trilaurate, in particular, as sold by TAIYO KAGAKU under the name Sunsoft Q-123Y-C.

In one embodiment, the polyglyceryl fatty ester surfactant is selected from the group consisting of polyglyceryl-2 laurate, polyglyceryl-10 dioleate (and) tocopherol, polyglyceryl-6 dicaprate, polyglyceryl-10 dioleate, polyglyceryl-10 trilaurate and combinations thereof.

At least one surfactant chosen from polyglyceryl fatty acid esters will typically be present in the composition in an amount of from about 0.2% to about 7.0% by weight, from about 0.25% to about 2.5% by weight, from about 1.0% to about 2.0% by weight or from about 2.0% to about 7%, based on the total weight of the composition.

Sunscreen Actives

The composition according to the invention may comprise at least one sunscreen active.

Examples of suitable sunscreen actives which may be used in the present invention include, but are not limited to, dibenzoylmethane derivatives such as butyl methoxydibenzoylmethane, also known as avobenzone, and commercially available under the tradenames Parsol® 1789, Eusolex® 9020, and Escalol® 517; octyl methoxycinnamate commercially available under the tradenames Eusolex® 2292, Parsol® MCX, and Univul® MC80; anthranilates; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. No. 5,237,071, U.S. Pat. No. 5,166,355, GB 2 303 549, DE 197 26 184 and EP 893 119; benzoxazole derivatives such as those described in patent applications EP 0 832 642; EP 1 027 883, EP 1 300 137 and DE 101 62 844; screening polymers and screening silicones such as those described especially in patent application WO 93/04665; dimers derived from α-alkylstyrene, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:

para-Aminobenzoic Acid Derivatives:

Examples of suitable para-Aminobenzoic acid derivatives include, but are not limited to, PABA, Ethyl PABA, Ethyl dihydroxypropyl PABA, Ethylhexyl dimethyl PABA sold in particular under the name "Escalol 507" by ISP, Glyceryl PABA, and PEG-25 PABA sold under the name "Uvinul P25" by BASF.

Salicylic Derivatives:

Examples of suitable salicylic derivatives include, but are not limited to, Homosalate sold under the name "Eusolex HMS" by Rona/EM Industries, Ethylhexyl salicylate sold under the name "Neo Heliopan OS" by Haarmann and Reimer, Dipropylene glycol salicylate sold under the name "Dipsal" by Scher, and TEA salicylate sold under the name "Neo Heliopan TS" by Haarmann and Reimer.

β,β-Diphenylacrylate derivatives:

Examples of suitable β,β-diphenylacrylate derivatives include, but are not limited to, Octocrylene sold in particular under the trade name "Uvinul N539" by BASF, and Etocrylene sold in particular under the trade name "Uvinul N35" by BASF.

Benzophenone Derivatives:

Examples of suitable benzophenone derivatives include, but are not limited to, Benzophenone-1 sold under the trade name "Uvinul 400" by BASF, Benzophenone-2 sold under the trade name "Uvinul D50" by BASF, Benzophenone-3 or Oxybenzone sold under the trade name "Uvinul M40" by BASF, Benzophenone-4 sold under the trade name "Uvinul MS40" by BASF, Benzophenone-5, Benzophenone-6 sold under the trade name "Helisorb 11" by Norquay, Benzophenone-8 sold under the trade name "Spectra-Sorb UV-24" by American Cyanamid, Benzophenone-9 sold under the trade name "Uvinul DS-49" by BASF, Benzophenone-12, and Diethylaminohydroxybenzoylhexyl benzoate sold under the trade name "Uvinul A Plus" by BASF, Benzylidenecamphor Derivatives:

Examples of suitable benzylidenecamphor derivatives include, but are not limited to, 3-Benzylidenecamphor manufactured under the name "Mexoryl SD" by Chimex, 4-Methylbenzylidenecamphor sold under the name "Eusolex 6300" by Merck, Benzylidenecamphorsulfonic acid manufactured under the name "Mexoryl SL" by Chimex, Camphor benzalkonium methosulfate manufactured under the name "Mexoryl SO" by Chimex, Terephthalylidenedicamphorsulfonic acid manufactured under the name "Mexoryl SX" by Chimex, and Polyacrylamidomethylbenzylidenecamphor manufactured under the name "Mexoryl SW" by Chimex.

Phenylbenzimidazole Derivatives:

Examples of suitable phenylbenzimidazole derivatives include, but are not limited to, Phenylbenzimidazolesulfonic acid sold in particular under the trade name "Eusolex 232" by Merck, and Disodium phenyl dibenzimidazole tetrasulfonate sold under the trade name "Neo Heliopan AP" by Haarmann and Reimer.

Phenylbenzotriazole Derivatives:

Examples of suitable phenylbenzotriazole derivatives include, but are not limited to, Drometrizole trisiloxane sold under the name "Silatrizole" by Rhodia Chimie, and Methylenebis(benzotriazolyl)tetramethylbutylphenol sold in solid form under the trade name "MIXXIM BB/100" by Fairmount Chemical, or in micronized form as an aqueous dispersion under the trade name "Tinosorb M" by Ciba Specialty Chemicals.

Triazine Derivatives:

Examples of suitable triazine derivatives include, but are not limited to, -Bis(ethylhexyloxyphenol)methoxyphenyl triazine sold under the trade name "Tinosorb S" by Ciba-Geigy, Ethylhexyltriazone sold in particular under the trade name "Uvinul T150" by BASF, Diethylhexylbutamidotriazone sold under the trade name "Uvasorb HEB" by Sigma 3V, and 2,4,6-tris(diisobutyl 4'-aminobenzalmalonate)-s-triazine.

Anthranilic Derivatives:

Examples of suitable anthranilic derivatives include, but are not limited to, Menthyl anthranilate sold under the trade name "Neo Heliopan MA" by Haarmann and Reimer.

Imidazoline Derivatives:

Examples of suitable imidazoline derivatives include, but are not limited to, Ethylhexyldimethoxybenzylidenedioxoimidazoline propionate.

Benzalmalonate Derivatives:

Examples of suitable benzalmalonate derivatives include, but are not limited to, Polyorganosiloxane containing benzalmalonate functions, for instance Polysilicone-15, sold under the trade name "Parsol SLX" by Hoffmann LaRoche.

4,4-Diarylbutadiene Derivatives:

Examples of suitable 4,4-diarylbutadiene derivatives include, but are not limited to, 1,1-Dicarboxy(2,2'-dimethylpropyl)-4,4-diphenyl-butadiene.

Benzoxazole Derivatives:

Examples of suitable benzoxazole derivatives include, but are not limited to 2,4-bis[5-(1-dimethylpropyl)benzoxazol-2-yl(4-phenyl)imino]-6-(2-ethylhexyl)imino-1,3,5-triazine sold under the name Uvasorb K2A by Sigma 3V.

Avobenzone: (trade names are Parsol 1789, Eusolex 9020, Escalol 517 and others, INCI Butyl Methoxydibenzoylmethane). It is a dibenzoylmethane derivative.

Octinoxate: Octyl methoxycinnamate (INCI) or octinoxate (USAN), trade names Eusolex 2292, Parsol MCX, Uvinul MC80.

The sunscreen actives suitable for use in the composition according to the present invention may also include mixtures of the above compounds.

The at least one sunscreen active is typically present in an amount of from about 0.1% to about 50% by weight, such as from about 5% to about 50% by weight, and from about 9% to about 30% by weight, based on the total weight of the composition.

It has also been unexpectedly discovered that the composition of the present invention is capable of carrying significant quantities of sunscreen active, i.e. greater than 10% by weight, based on the total weight of the composition, while at the same time remaining stable and being able to absorb quickly into the skin.

Auxiliaries

The composition according to the invention may comprise at least one dyestuff chosen especially from pigments, nacres, liposoluble dyes and water-soluble dyes, and mixtures thereof.

The term "pigments" should be understood as meaning white or coloured, mineral or organic particles of any shape, which are insoluble in the physiological medium and are intended to colour the composition.

The term "nacres" should be understood as meaning iridescent particles of any shape, especially produced by certain molluscs in their shell or else synthesized.

The term "dyes" should be understood as meaning generally organic compounds that are soluble in water or in fatty substances such as oils.

The pigments may be white or coloured, and mineral and/or organic. Among the mineral pigments that may be mentioned are titanium dioxides, optionally surface-treated, zirconium oxide and cerium oxide, and also zinc oxide, iron oxide (black, yellow or red) or chromium oxide, manganese violet, ultramarine blue, chromium hydrate and ferric blue and metal powders such as aluminium powder or copper powder.

An example that may be mentioned is micronized titanium dioxide powder surface-treated with a silica/aluminium hydroxide/alginic acid mixture, sold under the name MT-100AQ.

Among the organic pigments that may be mentioned are carbon black, pigments of D&C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment of the abovementioned type, and also nacreous pigments based on bismuth oxychloride.

The liposoluble dyes are, for example, Sudan red, D&C Red No 17, D&C Green No 6, β-carotene, soybean oil, Sudan brown, D&C Yellow No 11, D&C Violet No 2, D&C Orange No 5, quinoline yellow, annatto and bromo acids.

The dyestuffs may be present in an amount of from about 0.01% to about 30% by weight, such as from about 0.1% to about 20% by weight, such as from about 0.5% to about 15% by weight, and most preferably from about 0.5% to about 5% by weight, relative to the total weight of the composition.

In a known manner, the composition of the invention may also contain adjuvants that are common in cosmetics, such as humectants, preserving agents, antioxidants, complexing agents, solvents, fragrances, bactericides, odour absorbers, vitamins, moisturizers, self-tanning compounds and anti-wrinkle active agents. The amounts of these various adjuvants are those conventionally used in the field under consideration, for example from 0.01% to 20% of the total weight of the composition. Depending on their nature, these adjuvants may be introduced into the fatty phase, into the aqueous phase and/or into lipid vesicles.

The composition of the present disclosure may also contain cosmetically acceptable additives or adjuvants as well as cosmetic or dermatologic active agents. Representative additives and adjuvants include, for example, water-soluble or water-miscible solvents or co-solvents or oil-soluble or oil-miscible solvents or co-solvents. Suitable examples of additives and adjuvants include, but are not limited to, fatty alcohols, fatty amides, alkylene carbonates, glycols, lower alcohols (e.g. ethanol, propanediol), dispersion enhancing agents, polymers, thickening agents, stabilizers, moisturizers, humectants, colorants, fillers, chelating agents, antioxidants (e.g. BHT, tocopherol), essential oils, fragrances, dyes, neutralizing or pH-adjusting agents (e.g., citric acid, triethylamine (TEA) and sodium hydroxide), preservatives, bactericides, conditioning or softening agents (e.g., panthenol and allantoin), extracts, such as botanical extracts, or any other ingredient commonly used in cosmetics for this type of application. Additives and adjuvants may be present in the compositions in amounts generally ranging from about 0.01% to about 10% by weight. Examples of cosmetic active agents or dermatological active agents include free-radical scavengers, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in any water phase(s) or oil phase(s) that is/are present in the sunscreen composition (i.e., aqueous and/or fatty (oil) phase).

Of course, a person skilled in the art will take care to choose this or these optional additional compounds so that the advantageous properties intrinsically attached to the sunscreen composition in accordance with the invention are not, or not substantially, detrimentally affected by the envisaged addition or additions.

Needless to say, a person skilled in the art will take care to select this or of these optional additional compound(s), and/or the amount thereof, such that the advantageous properties of the composition according to the invention are not, or are not substantially, adversely affected by the envisaged addition.

The composition according to the invention finds its application in a wide variety of treatments, especially cosmetic treatments, of the skin, the lips and the hair, including the scalp, especially for treating, protecting or caring for the skin, the lips and/or the hair, and/or for making up the skin and/or the lips. It may also be intended for treating dry skin and/or dry lips, while at the same time delivering adequate SPF protection.

Stability

Compositions, according to the present disclosure, include a stable composition. By "stable" and grammatical variations thereof, it is meant that the compositions have maintained an aesthetically homogeneous phase, wherein there is no visually perceptible signs of phase separation, does not show a grainy texture and/or become inhomogeneous. The stability includes the ability to remain stable for a period of time, such as a time of greater than 8 weeks under conditions wherein the temperature ranges from about 4 degrees to about 45 degrees C.

Method

The sunscreen composition is prepared by combining the oil phase ingredients, including the polyglyceryl fatty acid esters, in a vessel and heating this oil phase while gently mixing until all solids dissolved, giving a homogeneous phase. The heating includes heating to a temperature from about 30° C. to 60° C. or about 45° C. The oil phase component is observed to verify that the components are dispersed and the mixing is continued while heating until fully homogeneous.

The following examples are intended to further illustrate the present invention. They are not intended to limit the invention in any way. Unless otherwise indicated, all parts are by weight.

EXAMPLES

TABLE 1

| Phase | INCI | HLB | 21A Ex. 1 | 21C Ex. 2 | 21E Ex. 3 | 21G Ex. 4 | 21H Ex. 5 |
|---|---|---|---|---|---|---|---|
| A | Butyloctyl Salicylate | | 3 | 3 | 3 | 3 | 3 |
| | Butyl Methoxydibenzoylmethane | | 1.5 | 1.5 | 1.5 | 1.5 | 1.5 |
| | Octocrylene | | 3.5 | 3.5 | 3.5 | 3.5 | 3.5 |
| | Ethylhexyl Salicylate | | 2.5 | 2.5 | 2.5 | 2.5 | 2.5 |
| | Homosalate | | 7.5 | 7.5 | 7.5 | 7.5 | 7.5 |
| | C12-15 Alkyl Benzoate | | 6.5 | 6.5 | 6.5 | 6.5 | 6.5 |
| | *Rosa Canina* Fruit Oil | | 4 | 4 | 4 | 4 | 4 |
| | *Oenothera Biennis* (Evening Primrose) Oil | | 2.5 | 2.5 | 2.5 | 2.5 | 2.5 |
| | *Prunus Amygdalus Dulcis* (sweet almond) oil | | 1.5 | 1.5 | 1.5 | 1.5 | 1.5 |
| | Dicaprylyl Carbonate | | 30 | 30 | 30 | 30 | 30 |
| | Tocopherol | | 0.5 | 0.5 | 0.5 | 0.5 | 0.5 |
| A1 | Hexyl Laurate | | 35 | 35 | 35 | 35 | 35 |
| B | Polyglyceryl-2 Laurate | 8.5-9.30 | 2 | | | | |
| | Polyglyceryl-10 dioleate (and) tocopherol | 11.9-12.19 | | 2 | | | |
| | Polyglyceryl-6 dicaprate | 12.55 | | | 2 | | |
| | Polyglyceryl-10 dioleate | 12.19 | | | | 2 | |
| | Polyglyceryl-10 trilaurate | 10.4-12.31 | | | | | 2 |
| | 18 WEEK STABILITY | | YES | YES | YES | YES | YES |

The compositions shown in Table 1 were prepared by heating the compositions of phases A and A1 (as shown in Table 1) to about 45° C. and adding phase B to heated composition and mixing until the polyglycerol fatty acid ester has dissolved into the composition. Thereafter, the composition was cooled to room temperature. Compatibility/Stability was evaluated in 1 week. "NO" denotes incompatibility, indicating that the surfactant failed and the composition separated. "YES" denotes that at 1 week the composition maintained stability.

TABLE 2

| Phase | INCI | HLB | 21 Comp. Ex. 1 | 21B Comp. Ex. 2 | 21D Comp. Ex. 3 | 21F Comp. Ex. 4 | L11226 149 6 Comp. Ex. 5 |
|---|---|---|---|---|---|---|---|
| A | Butyloctyl Salicylate | | 3 | 3 | 3 | 3 | 3 |
| | Butyl Methoxydibenzoylmethane | | 1.5 | 1.5 | 1.5 | 1.5 | 1.5 |
| | Octocrylene | | 3.5 | 3.5 | 3.5 | 3.5 | 3.5 |
| | Ethylhexyl Salicylate | | 2.5 | 2.5 | 2.5 | 2.5 | 2.5 |
| | Homosalate | | 7.5 | 7.5 | 7.5 | 7.5 | 7.5 |
| | C12-15 Alkyl Benzoate | | 6.5 | 6.5 | 6.5 | 6.5 | 6.5 |
| | *Rosa Canina* Fruit Oil | | 4 | 4 | 4 | 4 | 4 |
| | *Oenothera Biennis* (Evening Primrose) Oil | | 2.5 | 2.5 | 2.5 | 2.5 | 2.5 |
| | *Prunus Amygdalus Dulcis* (sweet almond) oil | | 1.5 | 1.5 | 1.5 | 1.5 | 1.5 |
| | Dicaprylyl Carbonate | | 30 | 30 | 30 | 30 | 30 |
| | Tocopherol | | 0.5 | 0.5 | 0.5 | 0.5 | 0.5 |
| A1 | Hexyl Laurate | | 35 | 35 | 35 | 35 | 35 |
| B | Polyglyceryl-5 Laurate | 10.9-13.70 | 2 | | | | |
| | Polyglyceryl-2 Oleate | 7.37 | | 2 | | | |
| | Polyglyceryl-2 Myristate | 8.54 | | | 2 | | |
| | Polyglyceryl-5 Oleate | 12.7-11.87 | | | | 2 | |
| | Polyglyceryl-3 polyricinoleate | 4 | | | | | 2 |
| | 1 WEEK STABILITY | | NO | NO | NO | NO | NO |

The compositions shown in Table 2 were prepared by the same process as described above with respect to Table 1. In addition, the 1 week stability was likewise determined using the same method described above with respect to Table 1.

TABLE 3

| Phase | INCI | 22 Ex 6 | 24 Ex. 7 | 26 Ex. 8 | 28 Ex. 9 | 29 Ex. 10 | 30 Ex. 11 | 31 Ex. 12 | 31A Ex. 13 | 32 Ex. 14 |
|---|---|---|---|---|---|---|---|---|---|---|
| A | Butyloctyl Salicylate | 3 | 3 | 3 | 3 | 3 | 3 | 3 | 3 | 3 |
| | Butyl Methoxydibenzoylmethane | 1.5 | 1.5 | 1.5 | 1.5 | 1.5 | 1.5 | 1.5 | 1.5 | 1.5 |
| | Octocrylene | 3.5 | 3.5 | 3.5 | 3.5 | 3.5 | 3.5 | 3.5 | 3.5 | 3.5 |
| | Ethylhexyl Salicylate | 2.5 | 2.5 | 2.5 | 2.5 | 2.5 | 2.5 | 2.5 | 2.5 | 2.5 |
| | Homosalate | 7.5 | 7.5 | 7.5 | 7.5 | 7.5 | 7.5 | 7.5 | 7.5 | 7.5 |
| | C12-15 Alkyl Benzoate | 6.5 | 6.5 | 6.5 | 6.5 | 6.5 | 6.5 | 6.5 | 6.5 | 6.5 |
| | *Rosa Canina* Fruit Oil | 4 | 4 | 4 | 4 | 4 | 4 | 4 | 4 | 4 |
| | *Oenothera Biennis* (Evening Primrose) Oil | 2.5 | 2.5 | 2.5 | 2.5 | 2.5 | 2.5 | 2.5 | 2.5 | 2.5 |
| | *Prunus Amygdalus Dulcis* (sweet almond) oil | 1.5 | 1.5 | 1.5 | 1.5 | 1.5 | 1.5 | 1.5 | 1.5 | 1.5 |
| | Dicaprylyl Carbonate | 30 | 30 | 30 | 30 | 30 | 30 | 30 | 30 | 30 |
| | Tocopherol | 0.5 | 0.5 | 0.5 | 0.5 | 0.5 | 0.5 | 0.5 | 0.5 | 0.5 |
| A1 | Hexyl Laurate | 32 | 32.7 | 30.7 | 30 | 36.5 | 29.7 | 33 | 33 | 34.8 |
| | Coconut Oil | | | 1.5 | | | | 2 | | |
| | Coconut Oil | | | | | | | | 2 | |
| | Squalane | | | | 2 | | | | | |
| B | Polyglyceryl-2 Laurate | | | | | | | | | |
| | Polyglyceryl-10 dioleate (and) tocopherol | 5 | 2 | 2 | 8 | 0.5 | 2 | 2 | 2 | 2 |
| | Polyglyceryl-6 dicaprate | | | | | | | | | |
| | Polyglyceryl-10 dioleate | | | | | | | | | |
| | Polyglyceryl-10 trilaurate | | | | | | | | | |
| C | Capryloyl Salicylic Acid | | 0.3 | 0.3 | | | 0.3 | | | |
| | Retinol | | 2 | 2 | | | 2 | | | |
| | Ethylhexyl Methoxycrylene | | | | | | 3 | | | |
| | Lavendar Oil | | | | | | | | | 0.1 |
| | *Pelargonium Graveolens* Flower Oil | | | | | | | | | 0.08 |
| | Rosemary Leaf Oil | | | | | | | | | 0.02 |

TABLE 4

|  | Ex. 2 | Comp Ex. 6* | Same |
|---|---|---|---|
| Greasier? | 4 | 10 | 0 |
| Shinier? | 1 | 10 | 3 |
| Absorbs Faster? | 9 | 4 | 1 |
| Preferred? | 9 | 5 | |

*Kiehl's Midnight Recovery

Table 4 shows an evaluation of the properties of the composition according to the present invention in comparison to a commercially available topical skin care product. The procedure includes placing the products in dropper bottles and 14 chemists evaluated the products indicating, when compared in the areas of greasiness, shininess, absorption and overall preference. The chemists evaluated an SPF containing oil (Example 2) compared with Kiehl's Midnight Recovery, available from L'Oreal. 9 out of 14 chemists preferred the SPF oil, with 10 out of 14 indicating that the SPF oil is faster absorbing.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A skin care composition comprising:
   (a) from about 10% to about 90% by weight, based on total weight of the composition, of a cosmetically acceptable oil;
   (b) a surfactant and
   (c) a sunscreen active;
   wherein the total amount of surfactant present in the composition is from about 0.25% to about 2.5% and consists of a polyglyceryl fatty acid ester having a hydrophile-lipophile balance value of from about 9 to about 12 selected from the group consisting of polyglyceryl-2 laurate, polyglyceryl-10 dioleate (and) tocopherol, polyglyceryl-6 dicaprate, polyglyceryl-10 dioleate, polyglyceryl-10 trilaurate and combinations thereof,
   wherein the composition is a stable emulsion, being characterized as having maintained an aesthetically homogeneous phase, wherein there are no visually perceptible signs of phase separation, and does not show a grainy texture and is not inhomogeneous, for a period of time of greater than 8 weeks under conditions wherein the temperature ranges from about 4 degrees to about 45 degrees C., and the composition confers improved skin absorption properties as compared with compositions having surfactant present in amounts greater than 2.5%, by weight.

2. The composition of claim 1, wherein the cosmetically acceptable oil is present in an amount of from about 50% to about 65% by weight, based on total weight of the composition.

3. The composition of claim 1, wherein the composition includes a combination of synthetic esters and natural oils.

4. The composition of claim 1, wherein the cosmetically acceptable oil includes a natural oil.

5. The composition of claim 4, wherein the natural oil is selected from the group consisting of *rosa canina* fruit oil, evening primrose oil, sweet almond oil, coconut oil and combinations thereof.

6. The composition of claim 1, wherein the cosmetically acceptable oil includes a fatty acid ester selected from the group consisting of dicaprylyl carbonate, hexyl laurate and combinations thereof.

7. The composition of claim 1, wherein the polyglyceryl fatty acid ester surfactant is present in an amount of from about 0.5% to about 2.0% based upon the weight of the composition.

8. The composition of claim 1, wherein the sunscreen active is selected from the group consisting of butyloctyl salicylate, butyl methoxydibenzoylmethane, octocrylene, ethylhexyl salicylate, homosalate and combinations thereof.

9. The composition of claim 1, wherein the sunscreen active includes each of butyloctyl salicylate, butyl methoxydibenzoylmethane, octocrylene, ethylhexyl salicylate, and homosalate.

10. A method of imparting sunscreen benefits onto a keratinous substrate by applying the composition of claim 1 onto said keratinous substrate.

11. A method for forming a skin care composition, the method comprising:
   combining a cosmetically acceptable oil and a sunscreen active;
   heating the cosmetically acceptable oil and the sunscreen active;
   adding from about 0.25% to about 2.5% by weight of a surfactant, based upon the weight of the composition, and mixing until a homogenous composition is formed;
   wherein the total amount of surfactant present in the composition is from about 0.25% to about 2.5% by weight and consists of a polyglyceryl fatty acid ester having a hydrophile-lipophile balance value of from about 9 to about 12 selected from the group consisting of polyglyceryl-2 laurate, polyglyceryl-10 dioleate (and) tocopherol, polyglyceryl-6 dicaprate, polyglyceryl-10 dioleate, polyglyceryl-10 trilaurate and combinations thereof;
   cooling to form the skin care composition,
   wherein the skin care composition is a stable emulsion being characterized as having maintained an aesthetically homogenous phase, wherein there is no visually perceptible signs of phase separation, and does not show a grainy texture and is not inhomogeneous for a period of time greater than 8 weeks under conditions wherein the temperature ranges from about 4 degrees to about 45 degrees C., and the composition confers improved skin absorption properties as compared with compositions having surfactant present in amounts greater than 2.5% by weight.

12. A skin care composition consisting of:
   (a) at least one cosmetically acceptable oil;
   (b) a surfactant;
   (c) at least one sunscreen active;
   (d) optionally one or more cosmetically acceptable additives selected from the group consisting of water-soluble and water-miscible solvents and co-solvents and oil-soluble and oil-miscible solvents and co-solvents, fatty alcohols, fatty amides, alkylene carbonates, glycols, lower alcohols, moisturizers, colorants, chelating agents, pigments, nacres, dyes, pH-adjusting agents, antioxidants, free-radical scavengers, vitamins, anti-elastase and anti-collagenase agents, peptides, steroids, trace elements, extracts of algae and of planktons, enzymes and coenzymes, flavonoids and ceramides, hydroxy acids, essential oils, fragrances, preservatives, bactericides, tocopherol, retinol, capryloyl salicylic acid, botanical extracts, and combinations thereof;
  wherein the total amount of surfactant present in the composition is from about 0.25% to about 2.5% and consists of a polyglyceryl fatty acid ester having a hydrophile-lipophile balance value of from about 9 to about 12 selected from the group consisting of polyglyceryl-2 laurate, polyglyceryl-10 dioleate (and) tocopherol, polyglyceryl-6 dicaprate, polyglyceryl-10 dioleate, polyglyceryl-10 trilaurate and combinations thereof, and
wherein the composition is a stable emulsion, being characterized as having maintained an aesthetically homogeneous phase, wherein there is no visually perceptible signs of phase separation, and does not show a grainy texture and is not inhomogeneous, for a period of time of greater than 8 weeks under conditions wherein the temperature ranges from about 4 degrees to about 45 degrees C., and the composition confers improved skin absorption properties as compared with compositions having surfactant present in amounts greater than 2.5%, by weight.

13. The skin care composition of claim 12, wherein the natural oil is selected from the group consisting of *rosa canina* fruit oil, evening primrose oil, sweet almond oil, coconut oil and combinations thereof, and wherein the cosmetically acceptable oil includes a fatty acid ester selected from the group consisting of dicaprylyl carbonate, hexyl laurate and combinations thereof.

14. The skin care composition of claim 12, wherein the sunscreen active is selected from the group consisting of butyloctyl salicylate, butyl methoxydibenzoylmethane, octocrylene, ethyl hexyl salicylate, homosalate and combinations thereof.

15. The skin care composition of claim 14, wherein the sunscreen active includes each of butyloctyl salicylate, butyl methoxydibenzoylmethane, octocrylene, ethylhexyl salicylate, and homosalate.

16. The skin care composition of claim 12, wherein the at least one cosmetically acceptable oil is present from about 10% to about 90% by weight, based on total weight of the composition, and wherein the at least one sunscreen active is present at greater than 10% by weight, based upon the weight of the composition.

17. The skin care composition of claim 1, wherein the sunscreen active is present at greater than 10% by weight, based upon the weight of the composition.

18. The skin care composition of claim 1, the composition including one or more cosmetically acceptable additives selected from the group consisting of water-soluble and water-miscible solvents and co-solvents and oil-soluble and oil-miscible solvents and co-solvents, fatty alcohols, fatty amides, alkylene carbonates, glycols, lower alcohols, moisturizers, colorants, chelating agents, pigments, nacres, dyes, pH-adjusting agents, antioxidants, free-radical scavengers, vitamins, anti-elastase and anti-collagenase agents, peptides, steroids, trace elements, extracts of algae and of planktons, enzymes and coenzymes, flavonoids and ceramides, hydroxy acids, essential oils, fragrances, preservatives, bactericides, tocopherol, retinol, capryloyl salicylic acid, botanical extracts, and combinations thereof.

* * * * *